(12) United States Patent
Carlson

(10) Patent No.: US 6,923,076 B2
(45) Date of Patent: Aug. 2, 2005

(54) FLUSHING A MULTI-PORT VALVE MANIFOLD

(75) Inventor: Stephen John Carlson, Shorewood, MN (US)

(73) Assignee: The BOC Group, Inc., Murray Hill, NJ (US)

( * ) Notice: Subject to any disclaimer, the term of this patent is extended or adjusted under 35 U.S.C. 154(b) by 391 days.

(21) Appl. No.: 10/215,751

(22) Filed: Aug. 9, 2002

(65) Prior Publication Data

US 2003/0056822 A1 Mar. 27, 2003

Related U.S. Application Data

(60) Provisional application No. 60/313,439, filed on Aug. 17, 2001.

(51) Int. Cl.[7] .............................................. G01N 1/00
(52) U.S. Cl. .................................... 73/864.81; 73/64.56
(58) Field of Search ......................... 73/863.33, 864.81, 73/865.5, 64.56; 436/175

(56) References Cited

U.S. PATENT DOCUMENTS

| | | | | |
|---|---|---|---|---|
| 4,993,271 A | * | 2/1991 | Vargason | 73/61.71 |
| 5,469,751 A | * | 11/1995 | Weiss et al. | 73/863.33 |
| 6,192,768 B1 | * | 2/2001 | Wallman et al. | 73/864.83 |

* cited by examiner

Primary Examiner—Robert Raevis
(74) Attorney, Agent, or Firm—David A. Hey

(57) ABSTRACT

A method for flushing gas pockets from a manifold that forms a part of a liquid sampling system that is compatible with a chemical-mechanical polishing system is described. A flushing liquid, e.g., ultra pure water, is introduced into, and expelled from, the manifold to expel gas pockets from the manifold. The method comprises the steps of opening a manifold vent, filling the manifold with the flushing liquid, and closing the vent to increase the velocity of the flushing liquid flowing through the manifold. The introduction of the flushing liquid is discontinued, and thereafter, resumed. The discontinuation and resumption steps are preferably repeated The manifold is thus flushed of gas pockets.

12 Claims, 4 Drawing Sheets

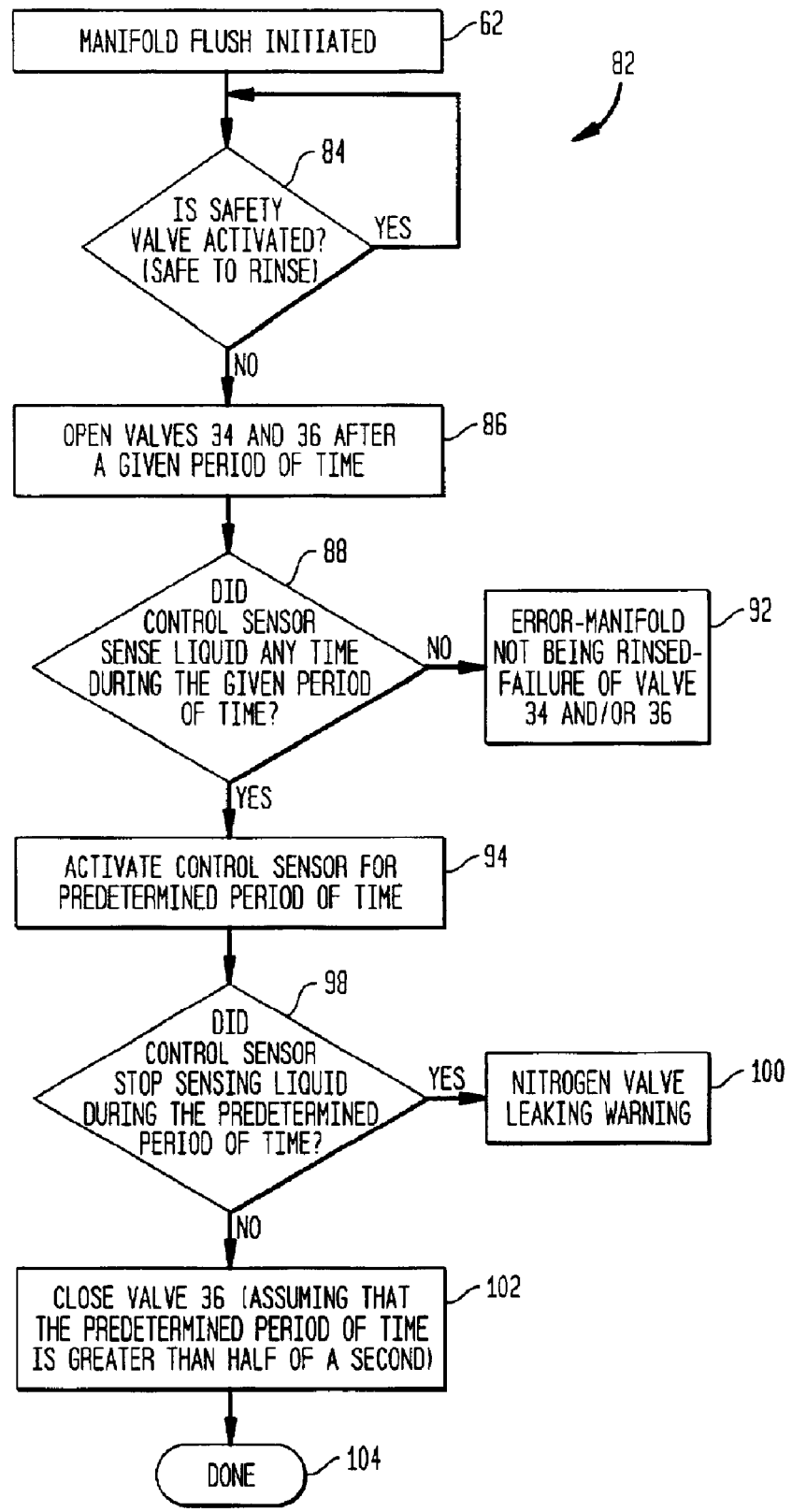

FLUSHING A MULTI-PORT VALVE MANIFOLD

CROSS-REFERENCE TO RELATED APPLICATIONS

Priority is claimed to U.S. provisional patent application Ser. No. 60/313,439 filed on Aug. 17, 2001.

BACKGROUND OF THE INVENTION

1. Field of the Invention

The invention relates to flushing gas pockets from a manifold. In one aspect, the invention relates to flushing gas pockets from a manifold that forms a part of a liquid sampling system while in another aspect, the invention relates to flushing gas pockets from a multi-port valve manifold disposed within a liquid sampling system that includes a sensor for monitoring the health of a slurry used in a chemical-mechanical polishing system, the sensor sensitive to gas pockets.

2. Description of the Related Art

A chemical-mechanical polishing (CMP) system is often employed in the microelectronics industry to contour and/or polish semiconductor wafers. These systems typically contain and employ a "slurry" which is cycled throughout the system such that the slurry contacts and/or impinges upon the wafers. As the cycling slurry impacts and/or passes over the wafers, the wafers are contoured and polished.

In order to maintain the consistency, performance, efficiency, and/or usefulness of the system, the "health" of the slurry must be maintained. Slurry instability, external contamination, or process conditions (e.g., shear-inducing pressure gradients, flow rates, and exposure to air) may all compromise slurry health. Thus, slurry properties (e.g., specific gravity, pH, weight percent solids, ionic contamination level, zeta potential, and particle size distribution (PSD)), are often closely monitored by sampling systems.

Of all the slurry health properties, perhaps the most important and frequently monitored is PSD. In the industry, PSD can be observed using a variety of instruments such as sensors, analyzers, and like devices (collectively referred to as sensors) that are commercially available from a host of manufacturers. For example, one such sensor is the AccuSizer 780/OL (AccuSizer) manufactured by Particle Sizing Systems (PSS) of Santa Barbara, Calif.

Unfortunately, while these PSD sensors are generally suitable for analyzing slurry, these sensors can possess disadvantages in some circumstances. Certain of these sensors are generally limited to sampling a single slurry at a single sampling point (i.e., a location within a CMP system from where a sample is taken). In other words, each CMP system, as well as each slurry used within that CMP system, would require a dedicated sensor. Since integrated circuit manufacturers, as well as others, often desire to analyze numerous different slurries, from multiple sampling points (i.e., locations), a one-to-one ratio of sensor to slurry would dramatically increases costs. Therefore, a liquid sampling system, using a single sensor, capable of monitoring one of a plurality of slurries from multiple sampling points was developed.

The liquid sampling system was built around a sensor to permit measurement of a number of different slurries, from multiple sample points, by utilizing a multi-port valve manifold. The multi-port valve manifold is operable, within the liquid sampling system, to selectively route any one of a number of different slurries, from a variety of locations, to a single sensor for PSD analysis.

While developing and testing the liquid sampling system, the need to sufficiently flush and/or rinse the multi-port valve manifold substantially free of gas pockets (i.e., bubbles) was revealed. The gas pockets, e.g., air, nitrogen, etc., are typically entrained in a liquid that is disposed within the manifold and/or clinging to surfaces (e.g., walls) of the manifold and associated components, hiding inside crevasses in the manifold, and otherwise trapped inside the manifold. If the gas pockets are permitted to pass through and/or proximate the sensor, the gas pockets can interfere with the operation and accuracy of the sensor. Moreover, since the gas pocket can contain, trap, hold, and/or support contaminants (e.g., debris, impurities, etc.), the contaminants can also interfere with the operation and accuracy of the sensor. As a result, if either or both of the gas pockets and the contaminants are permitted to pass through and/or proximate the sensor, the sensor and the liquid sampling system can return PSD results, data, and/or output that is skewed, unreliable and/or inaccurate.

Effectively removing gas pockets from a manifold is difficult, especially at relatively low pressures. Gas pockets have a tendency to cling to the surfaces (e.g., interior walls) of the manifold and associated components. Likewise, gas pockets often form in crevasses and other areas within the manifold that are difficult to access with flush or rinse liquids. Thus, a method of effectively flushing a manifold of residual gas pockets within a liquid sampling system is desirable.

SUMMARY OF THE INVENTION

In one embodiment of this invention, gas pockets are flushed from a manifold by a method comprising introducing a flushing liquid (e.g., ultra pure water) into the manifold through a manifold intake. Before, during or after the introduction of the flushing liquid, a vent on the manifold is opened to permit at least a portion of the gas pockets to escape through the vent. The flushing liquid, at least a portion of any initial contents (e.g., residual slurry from a previous sample) that may be present within the manifold at the start of the flush, and typically at least another portion of the gas pockets are discharged from the manifold through a manifold outlet. The manifold is then flooded with the flushing liquid such that the manifold is filled and remains filled with the flushing liquid while the flushing liquid continues to flow through it. With the flushing liquid flowing through the filled manifold, the vent is closed. This results in an increase in the velocity of the flushing liquid flowing through the manifold and this, in turn, results in the expulsion of additional gas pockets. The introduction or flow of the flushing liquid into the manifold is then discontinued (although the manifold remains filled with the flushing liquid), and this results in a decrease in pressure within the manifold). This decrease in pressure results in an expansion of the size of any residual gas pockets. Once sufficient time (e.g., typically several seconds) has passed to allow the residual gas pockets to expand, the introduction of the flushing liquid into the manifold is resumed. This resumption of the flushing liquid flow to the manifold results in the expulsion of the expanded gas pockets from the manifold.

The method can further comprise repeating the discontinuing and resuming steps to further expel gas pockets from the manifold. The repetition or "pulsing" of these two steps can occur once or any number of times, but typically diminishing returns in terms of gas pocket expulsion is achieved after only two or three repetitions.

BRIEF DESCRIPTION OF THE DRAWINGS

Embodiments of the invention are disclosed with reference to the accompanying drawings and are for illustrative purposes only. The invention is not limited in its application to the details of construction, or the arrangement of the components, illustrated in the drawings. The invention is capable of other embodiments or of being practiced or carried out in other various ways. Like reference numerals are used to indicate like components throughout the drawings.

FIG. 4 is a flowchart outlining the steps for performing a manifold flush procedure within the liquid sampling system of FIG. 1.

DETAILED DESCRIPTION OF THE PREFERRED EMBODIMENTS

Various items of equipment, such as fittings, valves, mountings, pipes, sensors, monitoring equipment, wiring, and the like have been omitted to simplify the description. However, such conventional equipment and its uses are known to those skilled in the art and can be employed as desired. Moreover, although the invention is described below in the context of slurries used in chemical-mechanical polishing processes, those skilled in the art will recognize that the invention can be employed with, and has applicability to, many other and different processes.

Figure 1:
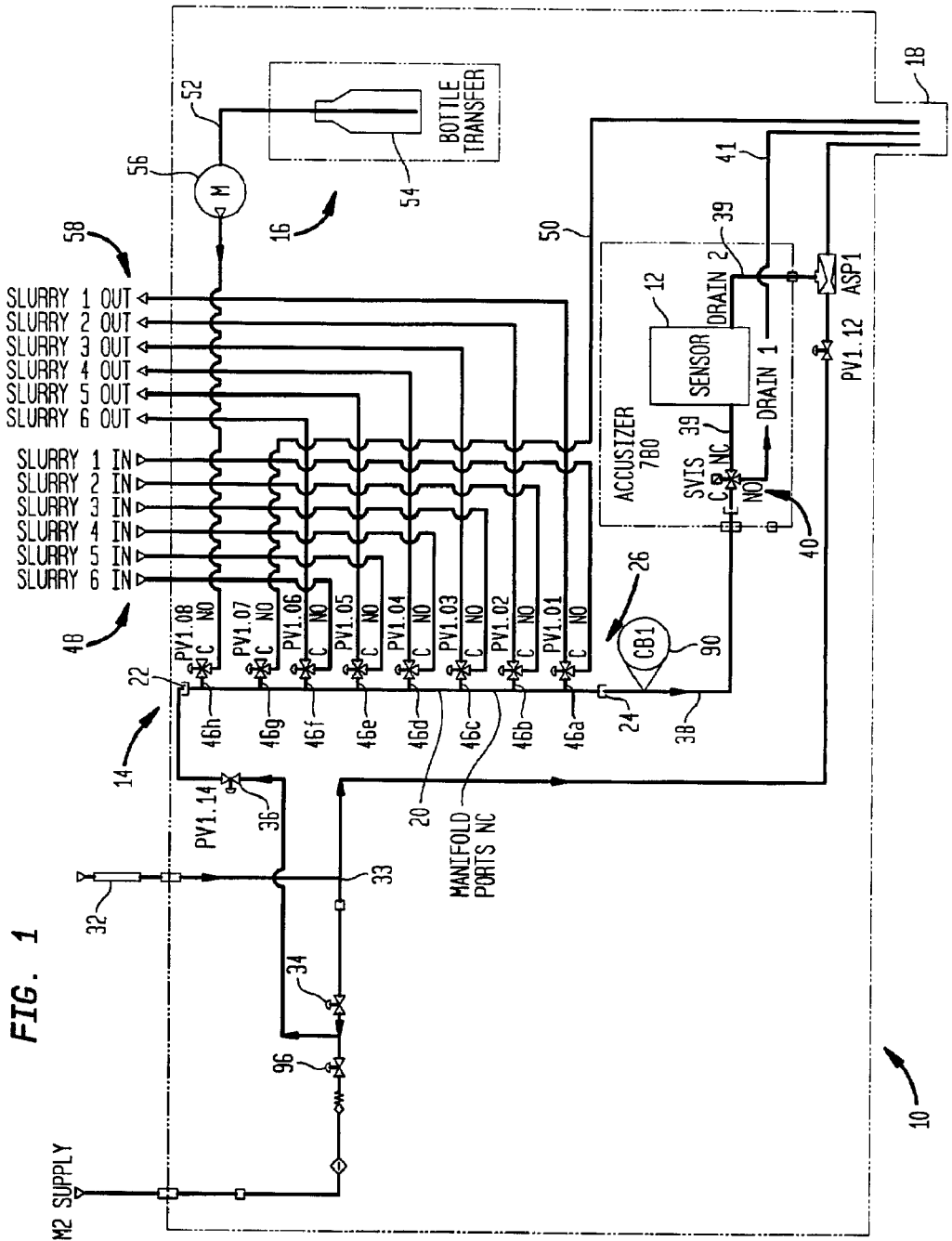
FIG. 1 is a schematic representation of a liquid sampling system comprising one embodiment of a manifold in accordance with one aspect of the present invention.

Referring to FIG. 1, a schematic representation of a liquid sampling system 10 is illustrated. In preferred embodiments, system 10 comprises a liquid sampling system known as the intelligent Slurry Particle Equipment (iSPEQ) system. The iSPEQ system is operable to monitor the health of chemical-mechanical polishing slurries. An exemplary description of the iSPEQ system is provided in commonly-owned, co-pending U.S. patent application Ser. No. 10/215,799, filed Aug. 9, 2002, entitled "Sampling and Measurement System with Multiple Slurry Chemical Manifold", and the contents and disclosure of that application are incorporated into the present application by this reference as if fully set forth herein.

System 10 comprises sensor 12, multi-port valve manifold 14, bottle sample station 16, and system drain 18. System 10 is operable to monitor and/or analyze a collected sample of slurry (or other liquid), that has been selectively and/or sequentially provided to the system. One example of slurry suitable for testing in system 10, and commonly used in CMP systems, would be Semi-Sperse SS-12 manufactured by Cabot Corporation, Boston, Mass. When operating system 10 slurry can be obtained from any number of sampling points (e.g., locations) within a single CMP system (not shown) and/or within several CMP systems. Also, slurry can be taken at any time during the "life" (i.e., period of use in a CMP system and/or systems) of the slurry.

For system 10 to monitor and/or analyze a slurry sample, the system relies on sensor 12. Sensor 12, as schematically illustrated in FIG. 1, comprises any sensor capable of monitoring and/or analyzing the health, and particularly the PSD, of slurry. Sensors that can be used in the practice of this invention are available from a host of different manufacturers, e.g., the AccuSizer 780/OL or the NICOMP 380/ZLS from Particle Sizing Systems (PSS) of Santa Barbara, Calif.; the LSTM 230 from Beckman Coulter of Fullerton, Calif.; the Lab CMP Slurry Monitor from Colloidal Dynamics of New South Wales, Australia; and the Liquilaz-SO5 or the SlurryChek from Particle Measuring Systems of Boulder, Colo. This list of acceptable and capable sensors, while certainly illustrative, is not intended to be exhaustive.

Although all of these sensors possess the ability to more than adequately monitor PSD, they can be fundamentally different in their manner of operation. Therefore, depending on the circumstances and manner of use, one sensor can be preferred over another for a given application. In certain embodiments of system 10, the AccuSizer 780/OL is a preffered sensor. The AccuSizer, a single optical particle counter, is described in detail in U.S. Pat. No. 5,835,211 (Wells, et. al.), and it is incorporated into the present application by this reference as if fully set forth herein.

Figure 2:
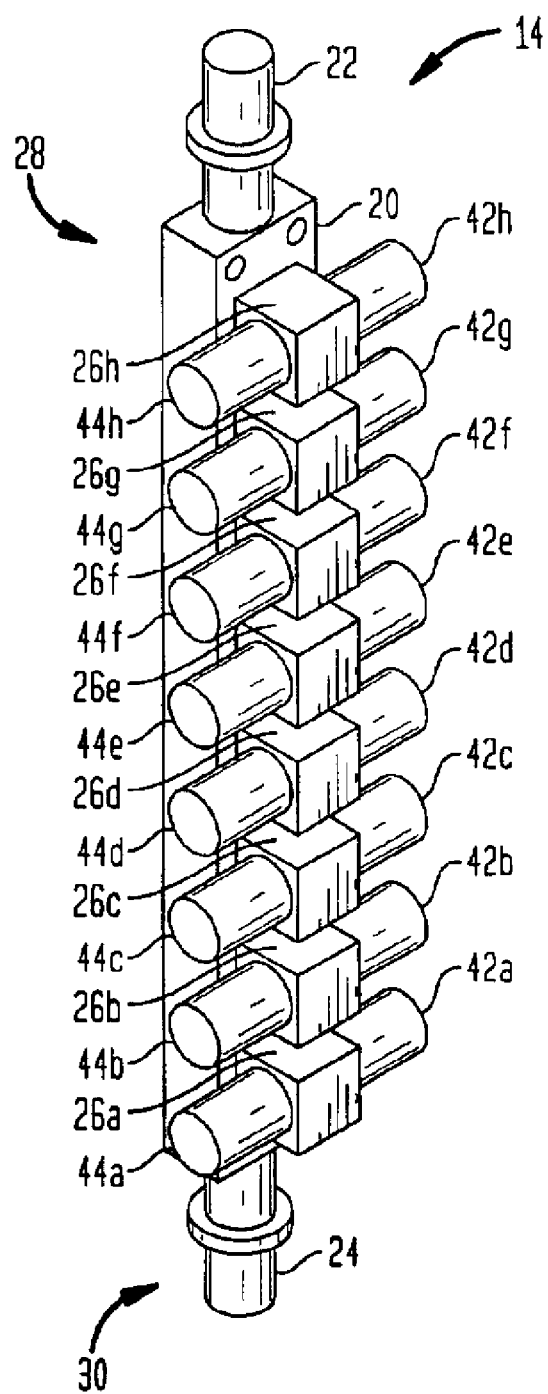
FIG. 2 is a perspective view of the manifold of FIG. 1.

Referring now to both FIGS. 1 and 2, multi-port valve manifold 14 comprises manifold body 20, manifold intake 22, manifold outlet 24, and a plurality of multi-port valves 26a–h (collectively 26). As shown in FIG. 2, manifold 14 has a top 28 and a bottom 30. In a preferred embodiment, manifold 14 is "vertically oriented" such that top 28 is vertically disposed above bottom 30 when the manifold is incorporated and/or employed within system 10. When manifold 14 is vertically oriented, manifold intake 22 is proximate top 28 and manifold outlet 24 is proximate bottom 30. As described in more detail below, the flushing of gas pockets from manifold 14 is often enhanced when manifold 14 is vertically oriented.

The pressure within manifold 14 will vary over the flush operation. Typically, the pressure within manifold 14 increases with an increase in the flow rate of the flushing liquid through the manifold, and it decreases with a decrease in the flow rate of the flushing liquid through the manifold.

Manifold body 20 comprises a structural member (e.g., a tube, a pipe, a channel, or the like) that has and defines internal surfaces or walls (not shown). Manifold body 20 is capable of permitting flushing fluid (e.g., ultra pure water) as well as other substances (e.g., debris, contaminants, slurry from a previous sample, and the like) to flow and/or pass through the manifold body.

Manifold intake 22 and manifold outlet 24 are connected to manifold body 20 proximate top 28 and bottom 30, respectfully, (i.e., at opposing ends) of manifold 14. Manifold intake 22 can deliver flushing liquid into manifold body 20 by receiving the liquid from supply line 32. The flushing liquid flows from and through supply line 32 to dividing point 33. At dividing point 33, the flushing liquid can be divided into two steams such that at least a portion of the flushing liquid flows through pressure valves 34 and 36, through manifold intake 22, and into manifold body 20 and manifold 14. Manifold outlet 24 expels flushing liquid and other substances from manifold body 20 and manifold 14. Therefore, the flushing liquid can pass through manifold 14, and preferably, capture those other substances remaining in the manifold. The flushing liquid, as well as other substances, are then discharged through manifold outlet 24 into manifold discharge line 38, through safety valve 40, and passed to either sensor line 39 or drain line 41. As such, the flushing liquid and other substances are either delivered to sensor 12 or system drain 18.

Although manifold 14 as shown in FIGS. 1 and 2 is equipped with eight multi-port valves 26 (e.g., three-way valves), any number of the multi-port valves can be used. In an exemplary embodiment, a pneumatic, eight-port, three-way valve manifold from Saint-Gobain Performance Plastic of Wayne, N.J. (formerly Furon Company) may be suitably employed as manifold 14. In the embodiment of FIG. 2, each of multi-port valves 26*a–h* comprises an intake port 42*a–h* (collectively 42), an outlet port 44*a–h* (collectively 44), and a body port 46*a–h* (collectively 46) (schematically shown in FIG. 1).

Referring to FIG. 1, intake ports 42*a–h* can be connected as desired to either a slurry supply line 48, a drain line 50, or a bottle sample line 52. In a preferred embodiment, intake ports 42*a–f* are each associated with a slurry supply line 48 and, therefore, can receive slurry from one of the respective slurry supply lines when the intake port is actuated or open. Thus, various samples of slurry can, in preferred embodiments, be selectively received into manifold 14 through one of intake ports 42*a–f* within valves 26*a–f*.

Intake ports 42*g–h* can be connected as desired to either drain line 50 or bottle sample line 52. In a preferred embodiment, as shown in FIG. 1, intake port 42*g* actually functions as an outlet (despite being labeled as an intake port). Thus, if necessary or desired, intake ports can be employed as outlet ports, and vise versa. Although illustrated in FIG. 1 as unconnected and/or unused, outlet ports 44*g–h* can be, if desired, connected to drain line 50 and bottle sample line 52, respectively, in lieu of the lines being connect to intake ports 42*g–h*.

Intake port 42*g*, in one embodiment, is associated with drain line 50, and can, therefore, permit the discharge of air, gas pockets, flushing liquid, slurry, and other substances from manifold 14 when the intake port is actuated or open. As such, intake port 42*g* can, and often does, operate as a vent for manifold 14. When operating as a vent, intake port 42*g* is typically located proximate top 28 of manifold 14.

Intake port 42*h*, in one embodiment, is associated with bottle sample line 50, and can, therefore, receive slurry from bottle transfer station 16 when the intake port is actuated or open. Bottle transport station 16 permits a sample of slurry from a remote location and/or unconnected CMP system to nonetheless be introduced into manifold 14 and, consequently, to sensor 12. In other words, slurry from bottle transfer station 16 can be selectively introduced into manifold 14.

Bottle sample station 16 comprises bottle 54 and pump 56. Pump 56 can be operated to draw slurry from bottle 54 such that a slurry sample can be delivered, through slurry sample line 52, to manifold 14. The delivered slurry sample from sample line 52 can be received by intake port 42*h* of valve 26*h*. In an alternative embodiment, an aspirator or other device capable of transporting a fluid (e.g., flushing liquid, slurry, nitrogen gas, and the like) may be substituted for pump 54.

Referring again to FIG. 1, outlet ports 44*a–f* are each associated with a slurry discharge line 58 and, therefore, can discharge slurry through one of the respective slurry discharge lines 58 when the outlet ports are actuated or open. Thus, various samples of slurry can be selectively expelled from manifold 14 through one of outlet ports 44*a–f* within valves 26*a–f*. In preferred embodiments, slurry is substantially continuously flowed from each slurry supply line 48 into an associated valve 26, and then it is discharged from the valve through an associated respective discharge line 58. As such, the slurry does not settle and/or precipitate in valves 26 and slurry lines 48, 58.

Finally, each body port 46*a–h* is integral or secured to, and associated with, manifold body 20. As such, each valve 26 is provided with a conduit (e.g., corridor) to manifold body 20. Therefore, when body ports 46 are actuated or open, any flushing liquid entering manifold 14 through manifold intake 22 can enter into each of valves 26 and, likewise, any slurry entering manifold 14 through one of intake ports 42*a–f* can enter into manifold body 20. In other words, valves 26 and manifold body 20 are in fluid communication with each other. Therefore, as shown in FIG. 1, slurry can be discharged from manifold 14 through manifold outlet 24 and/or through one of outlet ports 44*a–f*, as desired.

Should slurry be expelled from manifold 14 through manifold outlet 24, the slurry travels through manifold discharge line 38 until encountering safety valve 40 (e.g., a solenoid valve). During sampling and monitoring of the slurry, safety valve 40 can be actuated or opened to direct the slurry through sensor line 39 such that the slurry flows into, or proximate, sensor 12. As such, slurry can be monitored and/or analyzed by sensor 12. However, during flushing safety valve 40 can be actuated or opened to direct slurry through drain line 41 such that the slurry is discharged from system 10 through system drain 18.

In operation, system 10, using manifold 14, functions to selectively deliver a sample of one of a plurality of slurries, as desired, to sensor 12. Sensor 12 can then operate to monitor and/or analyze slurry health, including PSD. Sensor 12 (and/or system 10) can then generate output and data for review. Unfortunately, if manifold 14 is not sufficiently flushed substantially free of gas pockets (which can be entrained in a liquid, trapped in crevices within the manifold, clinging to the manifold and manifold components, and the like) prior to analyzing slurry health, the gas pockets and other substances within the manifold can dislodge, travel with the slurry, and enter or pass by sensor 14. If this occurs, data and/or output generated by sensor 12 and/or system 10 can be skewed, unreliable, and/or inaccurate.

Figure 3:
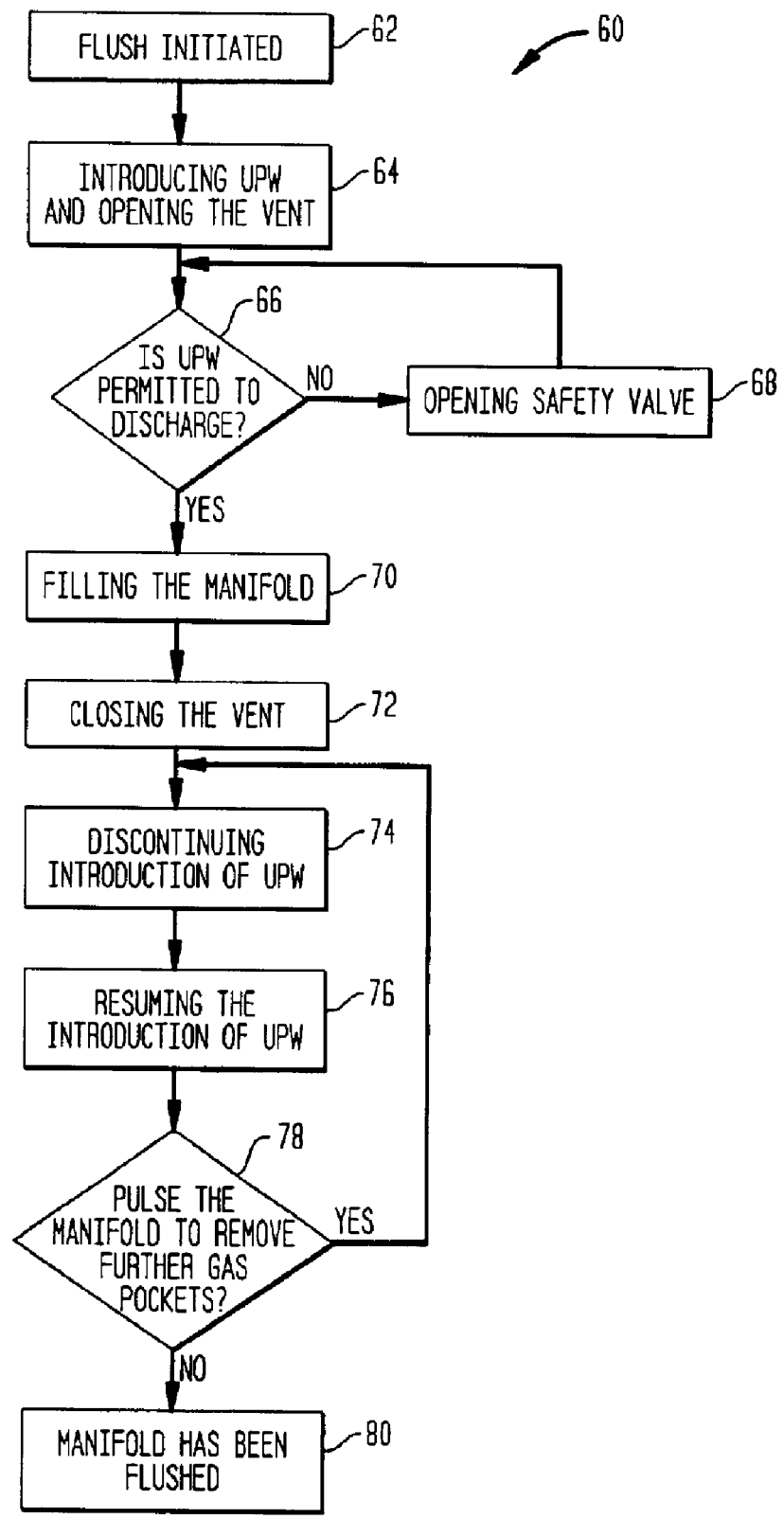
FIG. 3 is a flowchart outlining the steps for flushing the manifold of FIGS. 1 and 2.

In FIG. 3, a flowchart outlining one embodiment of a flushing procedure 60 for flushing manifold 14 is provided. Prior to employing flushing procedure 60, the contents of manifold 14 may or may not be known. Moreover, the volume of the contents may or may not be known. Therefore, manifold 14 can be empty or at least partially filled with one or more of the flushing liquid (e.g., ultra pure water), slurry, contaminants, gas pockets, etc. (collectively "initial contents") prior to initiation of flushing procedure 60. Flushing accomplishes the ultimate goal of removing gas pockets and/or gas pockets entrained in a liquid from within manifold 14.

To initiate flushing 62, a flushing liquid, for example an ultra pure water, from supply line 32 is introduced 64 into manifold 14 through manifold intake 22 and permitted 66 to discharge through manifold discharge line 38 at manifold outlet 24. In a preferred embodiment, the step of permitting 66 ultra pure water to discharge through manifold outlet 24 is performed by actuating 68, or keeping open, safety valve 40.

Simultaneously (or next), intake port 42*g* (i.e., vent) is opened 64 such that at least a portion of the gas pockets within the manifold are permitted to escape through the intake port. Since the gas pockets are typically buoyant, the gas pockets can rise up through manifold 14 and be expelled through intake port 42*g*. Also during opening step 64, at least a portion of the gas pockets can be expelled from manifold 14 by the flow of the flushing liquid through the manifold. As the flushing liquid travels from manifold intake 22 to manifold outlet 24, the flowing liquid can force a portion of the gas pockets out of the manifold at the manifold outlet.

Notably, while the flushing liquid is discharged from manifold outlet 24, and ultimately transferred to system drain 18, it can visually appear to be free of gas pockets.

However, the mere flow of the flushing liquid through manifold 14 does not ensure sufficient removal of gas pockets from within manifold 14. In fact, visually inspecting discharged flushing liquid to determine the presence or absence of gas pockets within manifold 14 is unreliable, and in some instances, deceptively misleading. As noted earlier, often gas pockets within manifold 14 cling to internal surfaces of or are otherwise trapped within the manifold. Therefore, continued steps are typically necessary to substantially and/or sufficiently flush the manifold.

Manifold 14 is next substantially, if not completely, filled and/or flooded 70 with flushing liquid. As the level, depth, or volume of the ultra pure water within manifold 14 increases, the flushing liquid lifts or pushes the gas pockets toward intake port 42g. Therefore, additional gas pockets can be removed from manifold 14. Still, further steps are typically desired to substantially and/or sufficiently flush manifold 14.

After manifold 14 is flooded with flushing liquid and while flushing liquid continues to flow through manifold 14, the intake port 42g can be closed 72. Upon closing 72 intake port 42g, the velocity of the flushing liquid flowing through manifold 14 increases. The increased velocity permits further removal of the gas pockets by, for example, dislodging the gas pockets from crevasses or otherwise "knocking" the gas pockets free from their clinging relationship with the internal surfaces of manifold 14, and the like. The dislodged gas pockets are expelled from manifold 14 at manifold outlet 24 by the force of the flowing flushing liquid with the increased velocity through the manifold. In one preferred embodiment, the step of closing 72 intake port 42g is performed about three seconds after the step of filling 70 the manifold.

After the intake port 42g is closed 72, introduction of the flushing liquid into manifold 14 is discontinued 74. By discontinuing 74 the delivery of the flushing liquid, pressure within manifold 14 decreases. As such, any gas pockets still remaining in manifold 14 are forced to expand, enlarge, and/or grow in size due to the pressure drop within the manifold. In one preferred embodiment, the step of discontinuing 74 the introduction of the flushing liquid is performed about three seconds after the step of closing 72 intake port 42g.

After the introduction of the flushing liquid has been discontinued 74, the introduction of the ultra pure water is resumed 76. Optionally, intake port 42g can also be re-opened. By resuming 76 the introduction of flushing liquid, a flow of the flushing liquid through manifold 14 is once again established. As such, the expanded gas pockets (or a substantial portion thereof) can be expelled from manifold 14. Thus, manifold 14, within system 10, can be substantially, sufficiently, and/or appropriately flushed. In one preferred embodiment, the step of resuming 76 the introduction of flushing liquid is performed about two seconds after the step of discontinuing 74 the introduction of the flushing liquid is performed.

In a preferred embodiment, the discontinuation and resumption steps are repeated at least once to remove even more gas pockets from the manifold. The repetition of these steps, also known as "pulsing", is identified as step 78 in FIG. 3. One exemplary embodiment calls for manifold 14 to be pulsed at least twice to substantially, sufficiently, and/or appropriately remove gas pockets from the manifold. After flushing, and preferably pulsing, are completed 80, manifold 14 should be sufficiently free of gas pockets to receive another slurry sample for transfer to sensor 12 for analysis.

In another embodiment, manifold 14 is disposed within system 10 and an iSPEQ process flow procedure 82, as illustrated in the flowchart of FIG. 4, is employed. The iSPEQ process flow procedure 82 is designed to rid manifold 14 of gas pockets, like those described above, other substances such as contaminants, debris, and the like, residing within the manifold that can be dislodged and removed with the ultra pure water. If these gas pockets and/or other substances were to enter or pass by sensor 12, then the sensor could provide an erroneous analysis or, possibly, be damaged.

Referring to FIG. 4, an iSPEQ process flow procedure 82 is used to maintain the safety of sensor 12 is illustrated. When manifold flush is initiated 62, a determination 84 is made as to whether safety valve 40 (FIG. 1), which is located near sensor 12, has been activated. In other words, a "safety check" determination 84 is made to ascertain whether it is safe to continue the manifold flushing procedure. Determination 84 comprises system 10 verifying that safety valve 40 is positioned to route flushing liquid, and any other substances flowing with the flushing liquid, through drain line 41. As such, the flushing liquid and/or other substances are expelled from system 10 at system drain 18 and, therefore, they are unable to enter or pass by sensor 12. Thus, sensor 12 can be spared from rendering an erroneous analysis or possible damage during the manifold flushing procedure.

However, should system 10 indicate that safety valve 40 is improperly positioned (i.e., valve 40 is positioned to route flushing liquid and/or other substances to sensor line 39), system 10 can actuate the safety valve to route the flushing liquid and/or other substances to drain line 41. Thus, system 10 can correct the improper or unsafe positioning of safety valve 40.

With safety valve 40 safely positioned, valves 34 and 36 can be opened 86. Opening 86 valves 34 and 36 permits flushing liquid to enter manifold 14 such that the manifold can be flushed pursuant to the manifold flushing procedure. After a predetermined period of time, e.g., valve 34 is closed. Subsequently, a determination 88 is made as to whether or not control sensor 90 (FIG. 1) has sensed any flushing liquid and/or other substances at any time during that period of time. If control sensor 90 did not sense any flushing liquid and/or other substances, system 10 renders 92 an error message indicating that manifold 14 is not rinsed or that at least one of valves 34 and 36 have failed. If control sensor 90 does detect flushing liquid and/or other substances during process flow procedure 82, then control sensor 90 is activated 94 for a predetermined period of time, preferably about ten seconds, to ensure nitrogen valve 96 (FIG. 1) is not leaking.

During the nitrogen valve leak check 98, if control sensor 90 stopped sensing flushing liquid and/or other substances during the predetermined period of time, then a nitrogen valve leak warning is issued 100. Alternatively, if control sensor 90 does not stop sensing liquid, then valve 36 (FIG. 1) is closed 102. This assumes, however, when valve 36 is to be closed 102, the predetermined period of time was greater than about half a second. Following the closing 102 of valve 36, process flow procedure 82 is completed 104 and, as such, other functions and features of system 10, which are not described in detail here, can be used and/or continued.

Within system 10, ultra pure water is typically and preferably employed as the flushing liquid. However, other grades of water can also be used in various embodiments of this invention, such de-ionized water and demineralized water. Ultra pure water, as known and conventionally used in integrated circuit production facilities throughout the United States, itself is available in various grades, e.g., c-grade ultra pure water, semiconductor grade ultra pure water, and the like. The composition of ultra pure water does and can vary from producer to producer, but a common guideline for ultra pure water can be found in "Ultra Pure Water Monitoring Guidelines 2000" from Balazs Analytical Laboratory in Sunnyvale, Calif.

Manifold 14 can experience other fluids and/or gases (e.g., nitrogen, oxygen, etc.) passing through the manifold during operation of system 10. Therefore, remnants of these other fluids and/or gases can be left behind in manifold 14. Moreover, a variety of valves, such as a two-way valve, a four-way valve, a three-way sampling valve, and the like, can be used in lieu of one or more of multi-port valves 26.

Commonly-owned, co-pending U.S. patent application Ser. No. 10/215,774 now U.S. Pat. No. 6,783,429 entitled "An Apparatus and Method for Sampling a Chemical-Mechanical Polishing Slurry", filed on Aug. 9, 2002, and U.S. patent application Ser. No. 10/322,238 entitled "Dilution Apparatus And Method of Diluting A liquid Sample", filed on Dec. 18, 2002, disclose other and various embodiments and components within a liquid sampling system that are compatible with a chemical mechanical polishing system and, therefore, the contents and disclosure of these applications are incorporated in to the present application by reference as if fully set forth herein.

Despite any methods being outlined in a step-by-step sequence, the completion of acts or steps in a particular chronological order is not mandatory. Further, elimination, modification, rearrangement, combination, reordering, or the like, of acts or steps is contemplated and considered within the scope of the description and appended claims.

While the flushing method is described in terms of a multi-port valve manifold, and more specifically a multi-port valve manifold for use within the iSPEQ slurry sampling system, the inventors contemplate that the method is equally applicable to other components and systems and may have other practical applications. Furthermore, while the present invention has been described in terms of preferred embodiments, equivalents, alternatives, and modifications, aside from those expressly stated, are possible and within the scope of the appended claims.

What is claimed is:

1. A method of flushing a manifold that (i) forms a part of a liquid sampling system, and (ii) contains gas pockets, the method comprising:
   introducing a flushing liquid into the manifold through a manifold intake, the flushing liquid introduced at a predetermined velocity;
   opening a vent on the manifold;
   discharging at least a portion of the flushing liquid through a manifold outlet;
   continuing to introduce the flushing liquid into the manifold such that the manifold is flooded;
   closing the vent while the manifold remains flooded and the flushing liquid continues to flow through the manifold;
   discontinuing the introduction of the flushing liquid into the manifold for a period of time sufficient to allow at least a portion of any remaining gas pockets within the manifold to expand in size; and
   resuming the introduction of the flushing liquid into and through the manifold such that the expanded gas pockets are substantially flushed from the manifold.

2. The method of claim 1 wherein the method further comprises repeating the discontinuing step and the resuming step.

3. The method of claim 1 wherein the flushing liquid comprises water.

4. The method of claim 3 wherein the water is ultra pure water.

5. The method of claim 1 wherein the gas pockets comprise at least one of air and nitrogen.

6. The method of claim 1 wherein the resuming step continues until the pressure within the manifold is substantially the same as the pressure outside the manifold.

7. The method of claim 1 wherein the manifold is vertically oriented within the sampling system, the manifold thus having a top and a bottom.

8. The method of claim 7 wherein the vent is located proximate the top of the manifold.

9. A method of flushing a manifold that (i) forms a part of a liquid sampling system that includes a sensor for monitoring a slurry used in a chemical-mechanical polishing system, and (ii) contains gas pockets, the method comprising:
   introducing ultra pure water into the manifold through a manifold intake, the flushing liquid introduced at a predetermined velocity, and opening a vent on the manifold;
   discharging the ultra pure water from the manifold through a manifold outlet;
   continuing to introduce the ultra pure water into the manifold such that the manifold is flooded;
   increasing the velocity of the ultra pure water flowing through the manifold by closing the vent;
   discontinuing the introduction of the flushing liquid into the manifold for a period of time sufficient to allow at least a portion of any remaining gas pockets within the manifold to expand in size; and
   resuming the introduction of the ultra pure water into the manifold such that the expanded gas pockets are substantially flushed from the manifold.

10. The method of claim 9 further comprising repeating the discontinuing and resuming steps.

11. The method of claim 9 wherein the sensor comprises an optical particle counter.

12. The method of claim 9 further comprising re-opening the vent simultaneously with the resuming step.

* * * * *